United States Patent [19]

Hunt

[11] Patent Number: 5,549,894
[45] Date of Patent: Aug. 27, 1996

[54] DISINFECTON FORMULATIONS AND METHODS USING D-ENANTIOMERIC ANTI-MICROBIAL PEPTIDES

[75] Inventor: Terrence J. Hunt, Moreno Valley, Calif.

[73] Assignee: Allergan, Inc., Irvine, Calif.

[21] Appl. No.: 182,993

[22] Filed: Jan. 18, 1994

[51] Int. Cl.$^6$ .......................... A61K 38/48; A61K 37/00
[52] U.S. Cl. ...................... 424/94.64; 424/94.63; 514/2; 514/912
[58] Field of Search ................ 514/2, 912; 424/94.63, 424/94.64

[56] References Cited

U.S. PATENT DOCUMENTS

| Re. 32,672 | 5/1988 | Huth et al. | 252/95 |
|---|---|---|---|
| 3,910,296 | 10/1975 | Karageozian et al. | 134/2 |
| 4,029,817 | 6/1977 | Blanco et al. | 424/329 |
| 4,407,791 | 10/1983 | Stark | 424/80 |
| 4,525,346 | 6/1985 | Stark | 424/80 |
| 4,614,549 | 9/1986 | Ogunbiyi et al. | 134/19 |
| 4,758,595 | 7/1988 | Ogunbiyi et al. | 514/635 |
| 5,096,607 | 3/1992 | Mowrey-McKee et al. | 252/106 |

OTHER PUBLICATIONS

Wade et al., *All–D Amino Acid–Containing Channel–Forming Antibiotic Peptides*, Proc. Natl. Acad. Sci. USA 87, 4761–4765 (Jun. 1990).

Bessalle et al., *All–D–magainin: Chirality, Antimicrobial Activity and Proteolytic resistance*, FEBS Letters 274, No. 1,2, 151–155 (Nov. 1990).

*Primary Examiner*—Zohreh Fay
*Attorney, Agent, or Firm*—Jeffer, Mangels, Butler & Marmaro LLP

[57] ABSTRACT

A method for disinfecting a contact lens, includes the step of contacting the lens with an effective amount of at least one D-enantiomeric anti-microbial agent for a period of time sufficient to disinfect the lens. A proteolytic enzyme can be used in conjunction with the anti-microbial agent for combined disinfection and cleaning. Contact lens disinfecting compositions comprising a D-enantiomeric anti-microbial agent are also provided.

17 Claims, No Drawings

DISINFECTON FORMULATIONS AND METHODS USING D-ENANTIOMERIC ANTI-MICROBIAL PEPTIDES

FIELD OF THE INVENTION

The present invention relates to methods and compositions for disinfecting a contact lens. In particular, the present invention relates to the use of an anti-microbial agent for disinfection of the lens.

BACKGROUND OF THE INVENTION

Contact lenses require an effective disinfection regimen to kill any harmful microorganisms that may be present or grow on the lenses, and thus pose a danger of serious eye infections and other health problems for the user. This is particularly true with respect to contact lenses made from hydrophilic materials. Harmful organisms which may be present on contact lenses or other eye care products such as lens cases include *Serratia marcescens, Staphylococcus epidermidis, Pseudomonas aeruginosa,* and *Candida albicans*. Likewise, other products, such as eye care solutions, which are susceptible to contamination by harmful organisms must be disinfected prior to use.

A number of methods for disinfecting contact lenses have been proposed, including the use of high temperatures, oxidative chemicals, and antimicrobial agents. U.S. Pat. Nos. 4,407,791 and 4,525,346 show the polyquaternary ammonium contact lens disinfecting agent 1-tris(2-hydroxyethyl)ammonium-2-butenyl- 4-poly[1-dimethyl ammonium-2-butenyl]-ω-tris(2-hydroxyethyl)ammonium chloride salt. European patent application 89810477.3 shows the disinfecting agent dodecyl-dimethyl-(2-phenoxyethyl)-ammonium bromide. U.S. Pat. No. 4,029,817 assigned to Allergan, Inc. shows the contact lens disinfecting agent tallow triethanol ammonium chloride. U.S. Pat. No. 4,758,595 shows the hexamethylene biguanide contact lens disinfecting agent.

Other types of agent have been examined for anti-microbial activity in vitro. For example, various surface-active peptides have been studied. Some of these peptides require a specific conformation. Others, such as cationic wide-range cytolytic peptides, are less reliant on specific conformations. These peptides appear to target the cellular lipid bilayer membrane, and to modulate membranal potential, permeability and function. One possible mechanism is thought to be formation of ion channels in the membrane, which causes lysis and cell death. Examples of the foregoing peptides include naturally occurring compounds such as cecropins, defensins, magainins, sarcotoxins, and melittins.

Certain cytolytic peptides have also been shown to possess anti-microbial activity in vitro as both the natural, all-L peptides and as the synthetic, all-D enantiomers. For example, in Wade et al., Proc. Natl. Acad. Sci. USA 87, 4761–4765 (June 1990), inhibition zone assays using thin agarose plates were carried out for all-D cecropin A, magainin 2 amide, melittin and certain cecropin-melittin hybrids. Standard anti-microbial activity assays were also carried out by Bessale et al., FEBS Letters 274, no. 1,2, 151–155 (November 1990) (hereinafter "Bessale I") for all-D magainin-2. The all-D enantiomers were also found to resist enzymatic cleavage, for example by trypsin, in vitro. No mention is made, however, of the use of these enantiomeric anti-microbial peptides in formulations such as disinfection formulations, nor of the use of such peptides in combination with proteolytic enzymes.

Contact lenses also require cleaning to remove soilants. For example, in the normal course of wearing contact lenses, tear film and debris consisting of proteinaceous, oily, sebaceous, and related organic matter have a tendency to deposit and build up on lens surfaces. As part of the routine care regimen, contact lenses must be cleaned to remove these tear film deposits and debris. If these deposits are not properly removed, both the wettability and optical clarity of the lenses is substantially reduced causing discomfort for the wearer.

The only safe and effective means found to date for removing protein build-up is the use of enzymes, whose hydrolytic activity reduces the proteinaceous materials to small, water soluble subunits. Particularly useful are proteolytic enzymes or proteases. U.S. Pat. No. 3,910,296 discloses the use of proteases for cleaning contact lenses.

New methods have been developed which can remove proteinaceous material from contact lenses while disinfecting the lenses. For example, U.S. Pat. No. 4,614,549 discloses a single-step method of cleaning and disinfecting contact lenses in aqueous solutions of proteolytic enzymes at temperatures of between 60° C. and 100° C. This method requires the use of electrical disinfecting apparatus and elevated temperatures. U.S. Pat. No. Re. 32,672, assigned to Allergan, Inc. discloses a method by which the lenses are immersed in a solution containing peroxide and a peroxide-active enzyme. Japanese patent application Showa 49-45012 discusses cleaning and sterilizing contact lenses by contacting the lens with an aqueous solution containing a protease and sterilizing agent such as triethanol tallow ammonium chloride, thimerosal and a wide range of reducing agents.

U.S. Pat. No. 5,096,607, to Mowrey-McKee et al., discloses a method for simultaneously cleaning and disinfecting contact lenses by contacting the lenses with a solution containing a proteolytic enzyme and a disinfecting agent which is either a polymeric quaternary ammonium salt or a biguanide, and adjusting the osmotic value of the solution to a level which does not inhibit the activity of the quaternary ammonium salt or the biguanide. This patent describes a wide range of useful proteolytic enzymes (in kind and amount) and a wide range of quaternary ammonium salts and biguanides (in kind and amount). None of the disinfecting agents are peptides, however, as such would be expected to be subject to attack by the proteolytic enzyme.

SUMMARY OF THE PREFERRED EMBODIMENTS

In accordance with one aspect of the present invention, there has been provided a method for disinfecting a contact lens comprising the step of contacting the lens with an effective amount of at least one D-enantiomeric anti-microbial agent for a period of time sufficient to disinfect the lens. Preferred D-enantiomeric anti-microbial agents are selected from D-enantiomeric peptides, such as cecropins, magainins and defensins. Derivatives of the foregoing agents possessing anti-microbial activity are also useful in the invention.

In a preferred embodiment, combinations of anti-microbial agents ("cocktails") are employed in the inventive method.

The inventive disinfecting method can also include simultaneous cleaning of the contact lens. Thus, according to another preferred embodiment, a solution is formed comprising an effective disinfecting amount of at least one D-enantiomeric anti-microbial agent, and an effective cleaning amount of a proteolytic enzyme. The contact lens is then contacted with this solution for a period of time sufficient to clean and disinfect the lens. Preferred enzymes include subtilisins.

According to another aspect of the present invention, a composition is provided for disinfecting a contact lens which comprises an effective amount of at least one D-enantiomeric anti-microbial agent. In a preferred embodiment, the composition further comprises a proteolytic enzyme for cleaning the lens while it is being disinfected.

According to a further aspect of the present invention, a method for disinfecting a solution is provided which comprises the step of adding to the solution an effective amount of a D-enantiomeric anti-microbial agent. In a preferred embodiment, the anti-microbial agent is added to an eye care solution.

According to yet another aspect of the present invention, there has been provided a method for disinfecting an article, such as a contact lens case, comprising the step of contacting the article with an effective amount of a D-enantiomeric anti-microbial agent for a period of time sufficient to disinfect the article. The anti-microbial agent can also be combined with an enzyme to carry out a disinfecting and cleaning operation.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

It has unexpectedly been discovered that D-enantiomeric anti-microbial agents are effective in formulations for disinfecting contact lenses, and that such agents furthermore are functional and effective when combined with proteolytic enzymes to simultaneously clean and disinfect contact lenses. Applications of methods of the present invention are not limited, however, to the disinfection of contact lenses. The inventive disinfection methods can also be adapted for use, for example, in cleaning other articles used for eye care, such as contact lens cases. Compositions according to the invention can also be used in treating burns, in other therapies requiring disinfection of a wound, and in simultaneous tissue hydrolysis and disinfection for scar reduction. The inventive disinfection and cleaning methods can be adapted, for example, to treat medical instruments. The inventive compositions can be solutions, for example, or other formulations such as gels or creams.

Useful anti-microbial agents according to the invention preferably are D-enantiomers of agents having anti-microbial activity which does not depend, or at least does not depend solely, upon interaction with specific cell surface receptors. Advantageously, the anti-microbial agents useful according to the invention include all-D enantiomeric forms of naturally occurring anti-microbial agents, preferably cytolytic peptides.

Particularly preferred are the D-enantiomeric forms of cecropins, magainins and defensins. Exemplary D-enantiomeric cecropins include the D-enantiomers of the peptides having the following amino acid sequences:

cecropin A:

Lys Trp Lys Leu Phe Lys Lys Ile Glu Lys Val Gly Gln Asn Ile Arg Asp Gly Ile Ile Lys Ala Gly Pro Ala Val Ala Val Val Gly Gln Ala Thr Gln Ile Ala Lys;

and cecropin B:

Lys Trp Lys Val Phe Lys Lys Ile Glu Lys Met Gly Arg Asn Ile Arg Asn Gly Ile Val Lys Ala Gly Pro Ala Ile Ala Val Leu Gly Glu Ala Lys Ala Leu Gly.

Cecropin D can also be employed in D-enantiomeric form.

D-enantiomeric cecropin derivatives having C-terminus modifications, substitutions, and/or truncations which either enhance or do not inhibit anti-microbial activity are also contemplated for use according to the present invention. Useful derivatives include D-enantiomeric cecropin A amide (CA-$NH_2$), and cecropin A with a C-terminal ethylenediamine-modified homoserine (CA-Hse-NH-Et-$NH_2$). The N-terminus portion of the cecropins is generally necessary for activity and is therefore less suitable for truncation, modification, or substitution. However, analogues resulting from substitution of amino acids with similar chemical characteristics to the original can be designed. Maintaining an amphipathic helical structure similar to the original peptide will result in conservation of anti-microbial activity. An example of a substitution analogue of cecropin B is Shiva-1:

Met Pro Arg Trp Arg Leu Phe Arg Arg Ile Asp Arg Val Gly Lys Gln Ile Lys Gln Gly Ile Leu Arg Ala Gly Pro Ala Ile Ala Leu Val Gly Asp Ala Arg Ala Val Gly.

D-enantiomeric Shiva-1, and other D-enantiomeric cecropin substitution analogs having anti-microbial activity, are contemplated as being useful according to the invention.

Exemplary useful D-enantiomeric magainins include the D-enantiomer of the native form, magainin 2. Useful derivatives include D-enantiomers of magainins having N-terminal positively charged chain extensions (e.g., $(Lys)_{10}$-magainin 2) and C-terminal amide groups (e.g., magainin 2-$NH_2$) which enhance the anti-microbial activity of the peptides. Additional magainins and magainin derivatives the D-enantiomers of which are contemplated for use according to the present invention are described in Zasloff et al., Proc. Natl. Acad. Sci. USA 85, 910–913 (February 1988); Zasloff, Proc. Natl. Acad. Sci. USA 84, 5449–5453 (August 1987); and Bessale et al., Antimicrobial Agents and Chemotherapy 36 (No. 2), 313–317 (February 1992), ("Bessale II") which are incorporated herein by reference.

D-enantiomeric defensins useful according to the invention include: HNP-1 (human neutrophil peptide 1):

Ala Cys Tyr Cys Arg Ile Pro Ala Cys Ile Ala Gly Glu Arg Arg Tyr Gly Thr Cys Ile Tyr Gln Gly Arg Leu Trp Ala Phe Cys Cys;

HNP-2:

Cys Tyr Cys Arg Ile Pro Ala Cys Ile Ala Gly Glu Arg Arg Tyr Gly Thr Cys Ile Tyr Gln Gly Arg Leu Trp Ala Phe Cys Cys;

HNP-3:

Asp Cys Tyr Cys Arg Ile Pro Ala Cys Ile Ala Gly Glu Arg Arg Tyr Gly Thr Cys Ile Tyr Gln Gly Arg Leu Trp Ala Phe Cys Cys;

NP-1 (rabbit neutrophil peptide 1):

Val Val Cys Ala Cys Arg Arg Ala Leu Cys Leu Pro Arg Glu Arg Arg Ala Gly Phe Cys Arg Ile Arg Gly Arg Ile His Pro Leu Cys Cys Arg Arg;

and the BNP-1 (bovine neutrophil peptide) sequence:

Arg Leu Cys Arg Val Val Ile Arg Val Cys Arg.

Other defensins and defensin analogs, such as those described in Selsted et al., J. Clin. Invest. 76, 1436–1439 (October 1985), and Kagan et al., Proc. Natl. Acad. Sci. USA 87, 210–214 (January 1990), the disclosures of which are incorporated herein by reference, are also useful in D-enantiomeric form according to the present invention.

The defensins are nonhelical pore formers, unlike the magainins and cecropins. However, analogues which mimic essential aspects of the native peptide conformation (assumed to be antiparallel β-sheet) will be most effective. Therefore, proper pairing and disulfide bonding of cysteine residues is necessary to ensure that the peptide is folded into the appropriate channel forming conformation.

Tachyplesins, such as tachyplesin I and II, and polyphemusins, such as polyphemusin I and II, are defensin-like peptides. See, e.g., Ohta et al., Antimicrobial Agents and Chemotherapy 36 (No. 7), 1460–1465 (July 1992), which is incorporated herein by reference. D-enantiomers of these peptides, and anti-microbially active derivatives thereof, are also contemplated as being useful according to the invention.

Other D-enantiomeric peptides, such as hybrids (peptides comprised of sequences from several anti-microbial classes), e.g., cecropin-melittin hybrids, and peptide analogs in which one or more of the D-amino acids corresponding to the L-amino acids of the all-L enantiomer are replaced with other D-amino acids, can also be used with advantage provided that they retain sufficient anti-microbial activity.

Exemplary hybrid peptides include cecropin A-(1-8)-melittin-(1-18)-NH$_2$:

Lys Trp Lys Leu Phe Lys Lys Ile Gly Ile Gly Ala Val Leu Lys Val Leu Thr Thr Gly Leu Pro Ala Leu Ile Ser-NH$_2$;

and cecropin A-(1-3)-melittin-(1-13)-NH$_2$:

Lys Trp Lys Gly Ile Gly Ala Val Leu Lys Val Leu Thr Thr Gly Leu-NH$_2$.

D-enantiomeric melittin itself, however, is unsuitable for use due to its high toxicity, like naturally occurring melittin.

The anti-microbial agents must be compatible with the contact lens being disinfected. The D-enantiomeric anti-microbial agents should be non-toxic to humans.

D-enantiomeric anti-microbial agents useful according to the invention can be prepared using techniques well known to those skilled in the art. D-enantiomeric peptides can be prepared by the solid-phase synthesis technique (see Merrifield, J. Am. Chem. Soc. 85, 214999–2154 (1963); Barany et al., The Peptides, vol. 2, pp. 1–284 (Gross et al., eds., Academic, New York 1979)). Exemplary processes for preparing D-enantiomeric anti-microbial peptides are given in Wade et al. and Bessale I, referred to above, which are incorporated herein by reference.

The D-enantiomeric anti-microbial agent utilized according to the present invention is employed in an effective amount to disinfect the contact lens being treated in a selected length of time. An effective disinfecting amount of the D-enantiomeric anti-microbial agent, or combination of agents, is an amount which will at least partially reduce the microorganism population on the lens being treated. Preferably, an effective disinfecting amount is that which will reduce the microbial burden by two log orders in four hours, and more preferably by one log order in one hour. Beneficially, a disinfecting amount is an amount which will eliminate the microbial burden on a contact lens when used in a contact lens care regimen which includes a recommended soaking time (FDA Chemical Disinfection Efficacy Test-July, 1985 Contact Lens Solution Draft Guidelines, incorporated herein by reference).

Typically the anti-microbial agent is present in a disinfecting solution with which the contact lens to be disinfected is placed in contact. In the working disinfecting solution, the anti-microbial agent preferably is present in a concentration from about 1 to about 500 ppm. An exemplary range of amounts of the D-enantiomeric anti-microbial agent in solution is about 0.0001% to 0.01% weight to volume. The contact lens is contacted with the solution containing the anti-microbial agent for the desired length of time, and is then rinsed, typically with a saline solution, prior to insertion into the eye of the user. If a solution, such as an eye care solution, is to be disinfected, the anti-microbial agent can be added in like amounts.

The anti-microbial agent can be introduced into the working solution in liquid form, i.e., in a prepared solution, or can be added in the form of a solid, i.e., tablet, powder, etc. Additional components may be added to or incorporated into the liquid or solid, or into the working solution, provided the additives do not substantially decrease the anti-microbial activity of the agent in the working solution. For example, components such as effervescing agents, stabilizers, buffering agents, chelating and/or sequestering agents, coloring agents, tonicity adjusting agents, surfactants and the like can be employed. In addition, binders, lubricants, carriers, and other excipients normally used in producing tablets may be so employed.

Examples of suitable buffering agents which may be incorporated into an anti-microbial tablet or solution include, but are not limited to, alkali metal salts such as potassium or sodium carbonates, acetates, borates, phosphates, citrates and hydroxides, and weak acids such as acetic and boric acids. Preferred buffering agents are alkali metal borates such as sodium or potassium borates. Additionally, other pH adjusting agents may be employed such as inorganic acids. For example, hydrogen chloride may be employed in concentrations suitable for ophthalmic uses. Generally, buffering agents are present in amounts to afford from about 0.01 to about 2.5% (w/v) of the solution, preferably from about 0.5 to about 1.5% (w/v). If used, sufficient quantities of buffering agent should be employed to maintain activity of the peptide and of any enzymes employed.

Effervescing agents are typically employed when the D-enantiomeric anti-microbial agent is provided in solid form. Examples of suitable effervescing agents include, but are not limited to, tartaric or citric acid used in combination with a suitable alkali metal salt such as sodium carbonate.

The tonicity adjusting agent which may be a component of the disinfecting solution and may optionally be incorporated into a tablet is employed to adjust the osmotic value of the final disinfecting solution to more closely resemble that of human tears and to maintain a suitable level for optimum activity by the antimicrobial agent.

Suitable surfactants can be either cationic, anionic, nonionic or amphoteric. Preferred surfactants are neutral or nonionic surfactants which may be present in amounts up to 5% (w/v). Examples of suitable surfactants include, but are not limited to, polyethylene glycol esters of fatty acids, polyoxypropylene ethers of $C_{12}$–$C_{18}$ alkanes and polyoxyethylene, polyoxypropylene block copolymers of ethylene diamine (i.e., poloxamine).

Examples of preferred chelating agents include ethylenediaminetetraacetic acid (EDTA) and its salts (disodium) which are normally employed in amounts from about 0.025 to about 2.0% (w/v). Other known chelating (or sequestering agents) such as certain polyvinyl alcohols can also be employed.

The binders and lubricants for tableting purposes and other excipients normally used for producing powders, tablets and the like, may be incorporated into tablet formulations within the present invention.

The D-enantiomeric anti-microbial agent(s) can also be combined with one or more additional known disinfecting agents. Suitable disinfecting agents are those generally employed in ophthalmic applications. Preferably such additional disinfecting agents are cationic or neutral, so that interaction between the various agents is minimized. Many such useful disinfecting agents are described, for example, in Huth et al., U.S. patent application Ser. No. 07/944,567, which is incorporated in its entirety herein by reference.

In another embodiment of the present invention, a D-enantiomeric antimicrobial agent can be combined with a proteolytic enzyme to produce a combined disinfecting/cleaning composition. The D-enantiomers are resistant to attack by the enzymes, and thus retain their activity in combination with the enzymes.

Suitable proteolytic enzymes for use according to the invention are the Bacillus-derived alkaline proteases generically called subtilisin enzymes. Microbial derived enzymes are disclosed in U.S. Pat. No. 4,690,773 incorporated herein by reference. Reference is also made to Keay, L, Moser, PW and Wildi, BS, "Proteases of the Genus Bacillus. II Alkaline Proteases," Biotechnology and Bioengineering, Vol. XII, pp. 213–249 (1970) and Keay, L and Moser, PW, "Differentiation of Alkaline Proteases form Bacillus Species", Biochemical and Biophysical Research Comm., Vol. 34, No. 5, pp. 600–604 (1969). Other exemplary enzymes useful according to the invention include papain, pancreatin, trypsin and chymotrypsin. Metallo-proteases, those enzymes which contain a divalent metal ion such as calcium, magnesium or zinc bound to the protein, may also be used. Combinations of enzymes can also be used.

The subtilisin enzymes include two sub-classes, subtilisin A and subtilisin B. In the subtilisin A grouping are enzymes derived from such species as *B. subtilis, B. licheniformis* and *B. pureills*. Organisms in this sub-class produce little or no neutral protease or amylase. The subtilisin B sub-class includes enzymes from such organisms as *B. subtilis, B. subtilis* var. *amylosacchariticus, B. amyloliquefaciens* and *B. subtilis* NRRL B3411. These organisms produce neutral proteases and amylases on a level about comparable to their alkaline protease production. Generally, the preferred enzymes are active proteolytic enzymes, with the most preferred being subtilisin A.

The identification, separation and purification of enzymes is an old art. Many identification and isolation techniques exist in the general scientific literature for the isolation of enzymes, including those enzymes having proteolytic and mixed proteolytic/amylolytic or proteolytic/lipolytic activity. The enzymes contemplated by this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention so long as they meet the criteria for stability and activity set forth herein. See Japanese Laid Open Application No. J6 0030-685 for one example of the production of proteases by recombinant DNA from *Bacillus subtilis*.

In the foregoing preferred embodiment of the present invention, an effective amount of enzyme is employed. An effective amount is that which removes a substantial portion of the proteinaceous deposits which occur during normal wear in a reasonable time. The precise amount of enzyme required to make an effective cleaner will depend on several factors including the activity of the enzyme, the purity of the enzyme, the amount of proteinaceous matter deposited on the lenses, the desired soaking period, the nature and concentration of the disinfecting agent, the specific type of lenses, as well as other well known factors.

The working solution should contain sufficient enzyme to provide between about 0.0001 and 0.5 Anson units per single lens treatment, preferably between 0.0008 and 0.036, more preferably between 0.001 and 0.012, optimally 0.012, Anson units per single lens treatment, in a 2–10 mL soak volume. Enzyme concentrations lower than these stated here probably will serve to clean the lens if sufficient time and heat is provided but such time may be so long and such heat so high as to be practically not useful in a usual lens cleaning and disinfecting regimen. The precise amount of enzyme will vary with the purity of the enzyme and will need to be finally determined on a lot-by-lot basis.

Enzyme activity is pH dependent. For any given enzyme, there will be a particular pH range in which that enzyme will function best. The determination of such range can readily be carried out by known techniques. It is preferred to manipulate the working solution to an optimum pH range for a given enzyme but such is not an absolute requirement. Generally, it is preferred that the enzyme be selected to have substantial activity at a pH between 6.5 and about 9.5 and even more preferably at between 6.9 to 7.9.

As with the disinfecting composition described above, the combined disinfecting/cleaning composition can be prepared in liquid form, to be added to a working solution, or in solid form such as tablets, powders, etc.

In practicing a method according to the present invention, the disinfecting or disinfecting/cleaning formulation, either in solid or liquid form, is usually dissolved in a predetermined amount of a working solution. When contact lenses are to be treated, the predetermined amount typically is 5–10 mL where a lens vial is used or 0.8 to 3.5 mL where the lens well of a lens case is used. The solution may be isotonic or hypotonic. This solution is then contacted with contact lens to be treated at ambient temperatures for a sufficient time to disinfect, or disinfect and clean, the lens. In another embodiment, the anti-microbial agent is added directly to a solution, such as a saline solution, which is to be disinfected. After an effective length of time, the solution is disinfected and ready for subsequent use.

Typically, the disinfecting, or disinfecting and cleaning, will take up to twelve hours (i.e., overnight). Effect times for any given composition within the present invention can be readily determined through routine testing.

Preferably, the contact lens treated according to the invention can be removed from the solution and used without the need for a separate neutralizing step. For example, contact lenses can be rinsed with the same aqueous multipurpose and disinfecting agent solution containing the disinfecting agent prior to insertion into the eye. There is preferably no need for a separate saline solution rinsing. Thus the multipurpose and disinfecting agent solution is preferably ophthalmically acceptable, i.e., it can be placed into a human eye without causing any substantial damage or harm.

When both a D-enantiomeric anti-microbial agent and a proteolytic enzyme are employed according to the present invention, the method of sequence of combining the components to make up the solution which contacts the lens to be treated will vary with the physical characteristics of the components. However, the order of addition is not critical to the practice of this invention. For example, the anti-microbial agent could be separately formulated as a tablet or powder and added to a working solution, or included directly in the working solution. Combinations of anti-microbial agents and proteolytic enzymes could be formulated as tablets or solutions. Optionally, separate solutions and/or tablets could be prepared containing the D-enantiomeric anti-microbial agent and the proteolytic enzyme, respectively. In one such embodiment, the enzyme and other dry components are formulated as a powder or tablet and dissolved in a solution comprising the anti-microbial agent. The contact lens to be treated is then introduced into this solution. Or, the lenses could already be in the anti-microbial agent solution when the enzyme (in aqueous form) is introduced.

A cleaning and disinfecting regimen within the scope of the present invention can include treatment with both the D-enantiomeric anti-microbial agent(s) alone and with a composition comprising the anti-microbial agent(s) and a proteolytic enzyme. In an exemplary regimen, the contact lens user employs a composition including the anti-microbial agent(s) on a daily basis, with weekly use of a combined anti-microbial agent/proteolytic enzyme composition. Use of the proteolytic enzyme on a daily basis would not be required. The proteolytic enzyme could, of course, be employed more than once per week, or with a lesser frequency.

The methods and compositions of the present invention are also useful in disinfecting, and optionally cleaning, other articles such as lens cases. Solutions, such as eye care solutions, can also be disinfected by addition thereto of an effective amount of a D-enantiomeric antimicrobial agent.

The following detailed Examples 1–7 are presented to illustrate tablet compositions for the D-enantiomeric anti-microbial agent.

EXAMPLE 1

| Ingredient | Mg/Tablet |
| --- | --- |
| D-cecropin | 0.1 |
| Di-Pac* | 40.0 |
| Polyethylene glycol 3350 | 4.0 |
| Povidone, PVP k-30 | 4.0 |

*Di-Pac is a compressible sugar. It is comprised of 97 w/w % sucrose and 3 w/w % maltodextrin. Di-Pac is available from Amstar Sugar Corporation and is distributed by Austin Chemical Co. in Illinois.

EXAMPLE 2

| Ingredient | Mg/Tablet |
| --- | --- |
| D-cecropin | 0.1 |
| Di-Pac | 40.0 |
| Sodium carbonate, anhydrous | 2.0 |
| Polyethylene glycol 3350 | 4.0 |
| Povidone, PVP k-30 | 4.0 |

EXAMPLE 3

| Ingredient | Mg/Tablet |
| --- | --- |
| D-cecropin | 0.1 |
| Subtilisin A* | 0.012 Au |
| Sodium carbonate, anhydrous | 52.0 |
| Sorbitol, FG instant | 40.0 |
| Polyethylene glycol 3350 | 6.0 |
| Tartaric acid | 7.0 |

*Subtilisin A MG 1.5 (Novo Industries of Copenhagen, Denmark) 1.9 Au/g

EXAMPLE 4

| Ingredient | Mg/Tablet |
| --- | --- |
| D-magainin | 0.1 |
| Sodium carbonate, anhydrous | 13.0 |
| Sorbitol, FG instant | 10.0 |
| Polyethylene glycol 3350 | 1.5 |
| Tartaric acid | 1.75 |

EXAMPLE 5

| Ingredient | Mg/Tablet |
| --- | --- |
| D-defensin | 0.1 |
| Sodium carbonate, anhydrous | 10.4 |
| Sorbitol, FG instant | 8.0 |
| Polyethylene glycol 3350 | 1.2 |
| Tartaric acid | 1.5 |

EXAMPLE 6

| Ingredient | Mg/Tablet |
| --- | --- |
| D-cecropin | 0.05 |
| D-defensin | 0.05 |
| Di-pac | 40.0 |
| Polyethylene glycol 3350 | 4.0 |
| Povidone, PVP k-30 | 4.0 |

EXAMPLE 7

| Ingredient | Mg/Tablet |
| --- | --- |
| D-cecropin | 0.05 |
| D-tachyplesin | 0.05 |
| Subtilisin A | 0.012 Au |
| Di-pac | 40.0 |
| Polyethylene glycol 3350 | 4.0 |
| Povidone, PVP k-30 | 4.0 |

The following Examples 8–12 are presented to illustrate anti-microbial agent and anti-microbial/protease solutions.

EXAMPLE 8

| Ingredient | % w/v |
| --- | --- |
| D-cecropin | 10 ppm |
| Edetate disodium USP | 0.05 |
| Sodium chloride USP | 0.37 |
| Hydrochloric acid | adjust to pH 7.5 |

EXAMPLE 9

| Ingredient | % w/v |
| --- | --- |
| D-cecropin | 10 ppm |
| Subtilisin A | 0.012 Au |
| Hydroxyethyl cellulose, NF | 0.65 |
| Sodium chloride, USP | 0.67 |
| Boric acid, NF | 0.39 |
| Sodium borate decahydrate, NF | 0.20 |
| Edetate disodium, USP | 0.127 |

EXAMPLE 10

| Ingredient | % w/v |
| --- | --- |
| D-defensin | 10 ppm |
| Papain | 0.012 Au |
| Boric acid | 0.39 |
| Edetate disodium | 0.1 |
| Sodium chloride | 0.40 |
| Sodium borate decahydrate, NF | 0.20 |
| Pluronic F-127 | 0.10 |

EXAMPLE 11

| Ingredient | % w/v |
| --- | --- |
| D-cecropin | 5 ppm |
| D-magainin | 5 ppm |
| Sodium chloride, USP | 0.37 |
| Tris | 1.2 |
| Tyloxapol | 250 ppm |
| EDTA | 0.05 |
| HCl | adjust pH to 7.5 |

EXAMPLE 12

| Ingredient | % w/v |
| --- | --- |
| D-defensin | 5 ppm |
| Sodium chloride, USP | 0.37 |
| Tris | 1.2 |
| Tyloxapol | 250 ppm |
| EDTA | 0.05 |
| PHMB (polyhexamethylene biguanide) | 0.5 ppm |
| HCl | adjust pH to 7.5 |

The following is an example of a cream formulation within the scope of the present invention, useful for therapeutic purposes such as burn treatment:

EXAMPLE 13

| Ingredient | % w/v |
| --- | --- |
| Sodium lauryl sulfate (30% paste) | 77.7 |
| Sodium stearate | 5.5 |
| Dimethicone copolyol | 0.5 |
| Cocamidopropyl betaine | 14.15 |
| Tar distillate | 1.1 |
| PPG-5 ceteth-10 phosphate | 1.0 |
| D-cecropin | 0.05 |

Other formulations within the scope of the present invention can easily be prepared in manners known to those skilled in the art.

What is claimed is:

1. A method for cleaning and disinfecting a contact lens comprising the step of contacting said lens with a solution comprising
   (a) an effective amount of at least one pharmaceutically acceptable D-enantiomer of a peptide having antimicrobial activity which is selected from the group consisting of D-enantiomers of cecropins, magainins, defensins, tachyplesins, polyphemusins, anti-microbially effective hybrids thereof and anti-microbially effective derivatives thereof,
   (b) an effective amount of a proteolytic enzyme, and
   (c) a pharmaceutically acceptable carrier for a period of time sufficient to clean and disinfect said lens.

2. The method of claim 1 wherein said D-enantiomer is selected from the group consisting of D-enantiomers of cecropin A, cecropin B, cecropin D, cecropin A amide (CA-NH$_2$), cecropin A with a C-terminal ethylenediamine-modified homoserine (CA-Hse-NH-Et-NH$_2$), Shiva-1, magainin-2, (Lys)$_{10}$-magainin 2, magainin 2-NH$_2$, HNP-1, HNP-2 HNP-3, NP-1, BNP-1, tachyplesin I, tachyplesin II, polyphemusin I, polyphemusin II, cecropin A-(1-8)-melittin-(1-18)-NH$_2$, and cecropin A-(1-3)-melittin-(1-13)-NH$_2$.

3. The method of claim 1 wherein said solution comprises from about 0.0001% to 0.01% weight to volume of said D-enantiomer.

4. The method of claim 1 wherein said proteolytic enzyme is selected from the group consisting of subtilisin, papain, pancreatin, trypsin and chymotrypsin.

5. The method of claim 1 wherein said solution comprises from about 0.0001% to 0.01% weight to volume of said D-enantiomer and from about 0.0001 to 0.5 Anson units of said proteolytic enzyme.

6. A composition for cleaning and disinfecting an article comprising
   (a) an effective amount of a pharmaceutically acceptable D-enantiomer of a peptide having antimicrobial activity which is selected from the group consisting of D-enantiomers of cecropins, magainins, defensins, tachyplesins, polyphemusins, anti-microbially effective hybrids thereof and anti-microbially effective derivatives thereof,
   (b) an effective amount of a proteolytic enzyme, and
   (c) a pharmaceutically acceptable carrier.

7. The composition of claim 6 wherein said D-enantiomer is selected from the group consisting of D-enantiomers of cecropin A, cecropin B, cecropin D, cecropin A amide (CA-NH$_2$), cecropin A with a C-terminal ethylenediamine-modified homoserine (CA-Hse-NH-Et-NH$_2$), Shiva-1, magainin-2, (Lys)$_{10}$-magainin 2, magainin 2-NH$_2$, HNP-1, HNP-2 HNP-3, NP-1, BNP-1, tachyplesin I, tachyplesin II, polyphemusin I, polyphemusin II, cecropin A-(1-8)-melittin-(1-18)-NH$_2$, and cecropin A-(1-3)-melittin-(1-13)-NH$_2$.

8. The composition of claim 7, comprising at least two different D-enantiomers.

9. The composition of claim 6 which is a solution.

10. The composition of claim 6 which is a solid.

11. The composition of claim 6 comprising about 0.0001% to 0.01% by weight of said D-enantiomer.

12. The composition of claim 6 comprising from about 0.0001% to 0.01% by weight of said D-enantiomer and from about 0.0001 to 0.5 Anson units of said proteolytic enzyme.

13. A method for disinfecting an eye care solution comprising the step of adding to said solution an effective amount of at least one pharmaceutically acceptable D-enantiomer of a peptide having antimicrobial activity which is selected from the group consisting of D-enantiomers of cecropins, magainins, defensins, tachyplesins, polyphemusins, anti-microbially effective hybrids thereof and anti-microbially effective derivatives thereof.

14. A method for cleaning and disinfecting an article comprising the step of contacting said article with (a) an effective amount of at least one pharmaceutically acceptable D-enantiomer of a peptide having antimicrobial activity which is selected from the group consisting of D-enantiomers of cecropins, magainins, defensins, tachyplesins, polyphemusins, anti-microbially effective hybrids thereof and anti-microbially effective derivatives thereof and (b) an effective amount of a proteolytic enzyme for a period of time sufficient to clean and disinfect said article.

15. The method of claim 13 wherein said D-enantiomer is selected from the group consisting of D-enantiomers of cecropin A, cecropin B, cecropin D, cecropin A amide (CA-NH$_2$), cecropin A with a C-terminal ethylenediamine-modified homoserine (CA-Hse-NH-Et-NH$_2$), Shiva-1, magainin-2, (Lys)$_{10}$-magainin 2, magainin 2-NH$_2$, HNP-1, HNP-2 HNP-3, NP-1, BNP-1, tachyplesin I, tachyplesin II, polyphemusin I, polyphemusin II, cecropin A-(1-8)-melittin-(1-18)-NH$_2$, and cecropin A-(1-3)-melittin-(1-13)-NH$_2$.

16. The method of claim 14 wherein said D-enantiomer is selected from the group consisting of D-enantiomers of cecropin A, cecropin B, cecropin D, cecropin A amide (CA-NH$_2$), cecropin A with a C-terminal ethylenediamine-modified homoserine (CA-Hse-NH-Et-NH$_2$), Shiva-1, magainin-2, (Lys)$_{10}$-magainin 2, magainin 2-NH$_2$, HNP-1, HNP-2 HNP-3, NP-1, BNP-1, tachyplesin I, tachyplesin II, polyphemusin I, polyphemusin II, cecropin A-(1-8)-melittin-(1-18)-NH$_2$, and cecropin A-(1-3)-melittin-(1-13)-NH$_2$.

17. The composition of claim 10 wherein said proteolytic enzyme is selected from the group consisting of subtilisin, papain, pancreatin, trypsin and chymotrypsin.

\* \* \* \* \*